(12) United States Patent
Miyakoshi

(10) Patent No.: US 9,821,099 B2
(45) Date of Patent: Nov. 21, 2017

(54) ARTIFICIAL-BLOOD-VESSEL CONNECTOR AND ARTIFICIAL-BLOOD-VESSEL UNIT

(71) Applicant: SUN MEDICAL TECHNOLOGY RESEARCH CORPORATION, Suwa-shi, Nagano (JP)

(72) Inventor: Takayuki Miyakoshi, Nagano (JP)

(73) Assignee: SUN MEDICAL TECHNOLOGY RESEARCH CORPORATION, Nagano (JP)

( * ) Notice: Subject to any disclaimer, the term of this patent is extended or adjusted under 35 U.S.C. 154(b) by 12 days.

(21) Appl. No.: 15/106,318

(22) PCT Filed: Dec. 27, 2013

(86) PCT No.: PCT/JP2013/085257
§ 371 (c)(1),
(2) Date: Jun. 20, 2016

(87) PCT Pub. No.: WO2015/097906
PCT Pub. Date: Jul. 2, 2015

(65) Prior Publication Data
US 2017/0000934 A1    Jan. 5, 2017

(51) Int. Cl.
| A61M 1/10 | (2006.01) |
|---|---|
| A61F 2/06 | (2013.01) |
| A61M 39/12 | (2006.01) |
| A61M 1/12 | (2006.01) |

(52) U.S. Cl.
CPC ............. *A61M 1/1008* (2014.02); *A61F 2/06* (2013.01); *A61M 39/12* (2013.01); *A61M 1/12* (2013.01); *A61M 2205/04* (2013.01); *A61M 2210/12* (2013.01)

(58) Field of Classification Search
CPC ....................................................... A61M 1/10
See application file for complete search history.

(56) References Cited

FOREIGN PATENT DOCUMENTS

JP          5288374 B2     9/2013

OTHER PUBLICATIONS

International Search Report in PCT/JP2013/085257, dated Apr. 1, 2014.

*Primary Examiner* — Matthew Schall
(74) *Attorney, Agent, or Firm* — Hauptman Ham, LLP

(57) ABSTRACT

An artificial-blood-vessel connector includes: a connector portion which includes a first cylindrical body portion where a male threaded portion and a flat surface portion where the male threaded portion is not formed are alternately formed along a circumferential direction of an outer peripheral surface, and a second cylindrical body portion to be fitted inside an artificial blood vessel; a ferrule which includes a cylindrical portion to be fitted on an outer peripheral surface of the second cylindrical body portion by way of the artificial blood vessel by being made to slide linearly on a surface of the artificial blood vessel, and a pawl plate portion in contact with the flat surface portion of the first cylindrical body portion; and a nut threadedly engageable with the male threaded portion of the first cylindrical body portion in a state where the nut covers the ferrule.

9 Claims, 9 Drawing Sheets

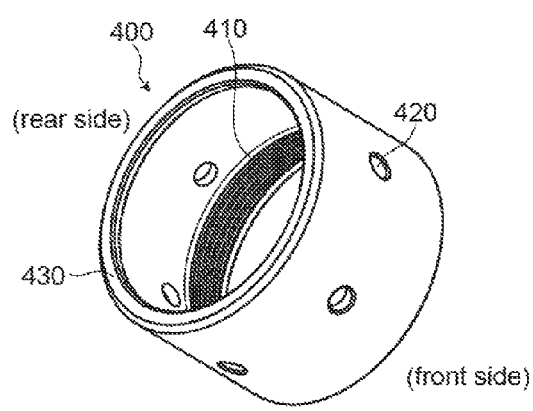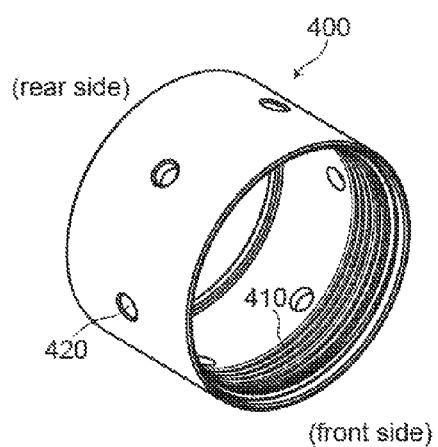
FIG.5A          FIG.5B
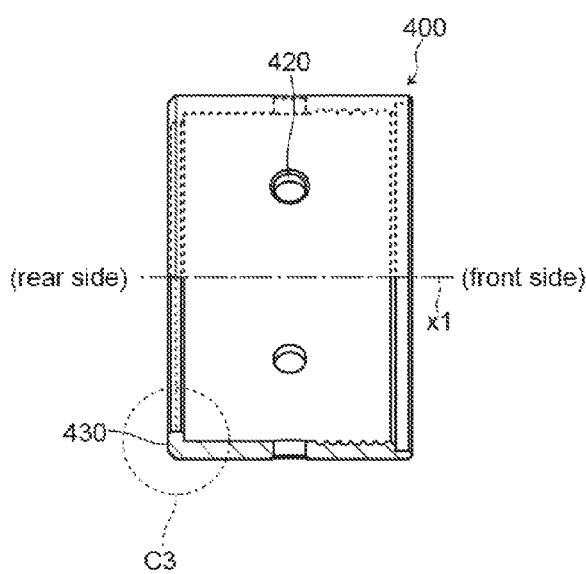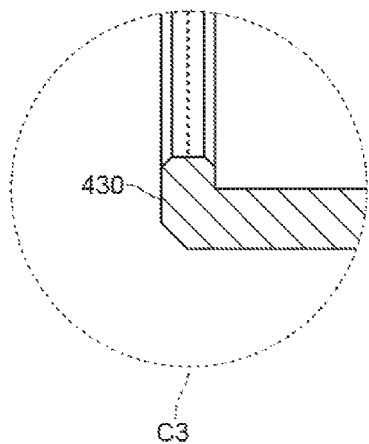
FIG.5C          FIG.5D

ARTIFICIAL-BLOOD-VESSEL CONNECTOR AND ARTIFICIAL-BLOOD-VESSEL UNIT

RELATED APPLICATIONS

The present application is a National Phase entry of International Application No. PCT/JP2013/085257, filed Dec. 27, 2013.

TECHNICAL FIELD

The present invention relates to an artificial-blood-vessel connector for connecting an artificial blood vessel to an object to be connected such as a blood pump or a cannula, and an artificial-blood-vessel unit where such an artificial-blood-vessel connector is mounted on an artificial blood vessel.

BACKGROUND ART

In connecting an artificial blood vessel to an object to be connected such as a blood pump or a cannula, an artificial-blood-vessel connector for connecting the artificial blood vessel to the object to be connected becomes necessary. As such an artificial-blood-vessel connector, conventionally, there have been known various types of artificial-blood-vessel connectors (see patent literature 1, for example).

FIG. 11 is a view for describing an artificial-blood-vessel connector 900 described in patent literature 1. As shown in FIG. 11, the artificial-blood-vessel connector 900 described in patent literature 1 includes: a joint member 910 having a male threaded portion 911; and a nut 920 having a female threaded portion 921 which is threadedly engageable with the male threaded portion 911 of the joint member 910. A tapered surface 912 whose diameter is narrowed gradually toward an end portion side of the joint member 910 is formed on an outer peripheral surface (an outer peripheral surface excluding the male threaded portion) of the joint member 910, and a tapered surface 922 having the same inclination as the tapered surface 912 formed on the joint member 910 is formed on an inner peripheral surface (an inner peripheral surface excluding the female threaded portion) of the nut 920. The joint member 910 is integrally formed with a cannula 930.

With respect to the artificial-blood-vessel connector 900 having such a configuration, the artificial-blood-vessel connector 900 can be connected to an artificial blood vessel 940 by making the female threaded portion 921 of the nut 920 threadedly engage with the male threaded portion 911 of the joint member 910 thus fastening the nut 920 to the joint member 910 in a state where the tapered surface 912 of the joint member 910 is fitted in the artificial blood vessel 940.

CITATION LIST

Patent Literature

Patent Literature 1: Japanese Patent No. 5288374

SUMMARY OF INVENTION

Technical Problem

However, in the artificial-blood-vessel connector 900 described in patent literature 1, at the time of making the female threaded portion 921 of the nut 920 threadedly engage with the male threaded portion 911 of the joint member 910 thus fastening the nut 920 to the joint member 910, an operation is performed where the nut 920 is rotated in a circumferential direction in a state where the tapered surface 922 of the nut 920 presses a surface of the artificial blood vessel 940. Accordingly, in the artificial-blood-vessel connector 900 described in patent literature 1, the artificial blood vessel is rubbed by a frictional force generated due to fastening the nut thus giving rise to a drawback that the artificial blood vessel is damaged.

Particularly, when the artificial blood vessel 940 is formed of a woven fabric made of resin fibers such as polyester fibers, the artificial blood vessel 940 has a small thickness and is weak against rubbing. Accordingly, when an operation is performed where the nut 920 is rotated in a circumferential direction in a state where the tapered surface 922 of the nut 920 presses the surface of the artificial blood vessel 940, a possibility that the artificial blood vessel 940 is damaged is further increased. In view of the above, it is important for an artificial-blood-vessel connector to be connected to an artificial blood vessel formed of a woven fabric made of resin fibers to have a structure which prevents a phenomenon that the artificial blood vessel is damaged by a frictional force generated due to fastening the nut.

With respect to the artificial-blood-vessel connector 900 described in patent literature 1, FIG. 11 shows the case where the connection between the joint member 910 and the artificial blood vessel 940 is performed by making the female threaded portion 921 of the nut 920 threadedly engage with the male threaded portion 911 of the joint member 910. Patent literature 1 also describes that the joint member 910 and the artificial blood vessel 940 can be locked to each other using pawl portions, concave and convex portions or the like, for example. It is true that in the case where the joint member 910 and the artificial blood vessel 940 are made to engage with each other by using the pawl portions or the concave and convex portions or the like and by not using a nut, it is unnecessary to perform an operation of rotating the nut 920 in a circumferential direction while pressing the tapered surface 922 of the nut 920 to the surface of the artificial blood vessel 940 and hence, it is possible to prevent a drawback "the artificial blood vessel is rubbed by a frictional force so that the artificial blood vessel is damaged". However, the mere locking of the joint member 910 and the artificial blood vessel 940 using the pawl portions, the concave and convex portions or the like without using the nut gives rise to a possibility that the locking is released due to some causes. Accordingly, the connection of the joint member 910 and the artificial blood vessel 940 using the pawl portions, the concave and convex portions or the like has a drawback that, compared to the connection of the joint member 910 and the artificial blood vessel 900 using the nut, the reliability in connection between the artificial blood vessel and the artificial-blood-vessel connector after the artificial-blood-vessel connector 900 is connected to the artificial blood vessel 940 is low.

The present invention has been made in view of the above-mentioned circumstances, and it is an object of the present invention to provide an artificial-blood-vessel connector which can prevent the occurrence of a damage on an artificial blood vessel and, at the same time, exhibits high reliability in connection between the artificial blood vessel and the artificial-blood-vessel connector to each other. It is also an object of the present invention to provide an artificial-blood-vessel unit where such an artificial-blood-vessel connector is mounted on an artificial blood vessel so that the artificial blood vessel which forms a part of the artificial-blood-vessel unit becomes a high quality artificial blood vessel having no damage, and the artificial-blood-vessel unit exhibits high reliability in connection between the artificial blood vessel and the artificial-blood-vessel connector.

Solution to Problem

[1] An artificial-blood-vessel connector of the present invention is an artificial-blood-vessel connector for connecting an artificial blood vessel to an object to be connected by being mounted on the artificial blood vessel, wherein assuming a side of the artificial-blood-vessel connector which faces the object to be connected as a front side, a side of the artificial-blood-vessel connector opposite to the front side as a rear side, and a direction along which a center axis of the artificial blood vessel extends as an axial direction, the artificial-blood-vessel connector includes: a connector portion which includes: a first cylindrical body portion where a male threaded portion and a flat surface portion where the male threaded portion is not formed are alternately formed along a circumferential direction of an outer peripheral surface; and a second cylindrical body portion which is formed on a rear-side end portion of the first cylindrical body portion, has an outer diameter smaller than an outer diameter of the first cylindrical body portion, and is configured to be fitted into the inside of the artificial blood vessel; a ferrule which includes: a cylindrical portion which is configured to be fitted on an outer peripheral surface of the second cylindrical body portion by way of the artificial blood vessel by being made to slide linearly toward the front side on a surface of the artificial blood vessel in a state where the second cylindrical body portion of the connector portion is fitted in the artificial blood vessel; and a pawl plate portion which is formed in a projecting manner along the axial direction from the cylindrical portion, and is brought into contact with the flat surface portion of the first cylindrical body portion; and a nut which includes a female threaded portion which is configured to threadedly engage with the male threaded portion of the first cylindrical body portion of the connector portion, and is configured to be connected to the connector portion by making the female threaded portion threadedly engage with the male threaded portion of the first cylindrical body portion in a state where the nut covers the ferrule when the second cylindrical body portion is fitted in the artificial blood vessel and the ferrule is mounted on the connector portion.

According to the artificial-blood-vessel connector of the present invention, the artificial-blood-vessel connector has the structure where the ferrule is mounted on the connector portion such that the ferrule slides linearly on the surface of the artificial blood vessel, and the nut is threadedly engaged with the connector such that the nut covers the ferrule. Accordingly, at the time of performing the fastening by making the female threaded portion of the nut threadedly engage with the male threaded portion of the connector portion, the nut cannot come into contact with the surface of the artificial blood vessel due to the presence of the ferrule. As a result, at the time of performing the fastening by rotating the nut, there is no possibility that rubbing occurs on the artificial blood vessel by a frictional force and hence, the occurrence of damage on the artificial blood vessel can be prevented preliminarily. Further, the nut is threadedly locked to the connector portion and hence, the reliability in connection between the artificial blood vessel and the artificial-blood-vessel connector can be increased.

As described above, the side of the artificial-blood-vessel connector which faces the object to be connected is assumed as the front side, and the side of the artificial-blood-vessel connector opposite to the front side is assumed as the rear side. In the case of the artificial-blood-vessel connector of the present invention, however, there may be also a case where the artificial-blood-vessel connector is mounted on sides of both end portions (referred to as "one end portion" and "the other end portion" hereinafter) of the artificial blood vessel respectively. In the case where the artificial-blood-vessel connector of the present invention is mounted on the side of one end portion and the side of the other end portion of the artificial blood vessel respectively in this manner, the side of one end portion and the side of the other end portion of the artificial blood vessel are independently considered. That is, with respect to the side of one end portion and the side of the other end portion of the artificial blood vessel, a side which faces an object to be connected is assumed as a front side, and a side which is opposite to the front side is assumed as a rear side respectively.

[2] In the artificial-blood-vessel connector of the present invention, it is preferable that the second cylindrical body portion of the connector portion include: a first flat outer peripheral surface portion which has an outer diameter of an outer peripheral surface thereof set to a fixed value in an axial direction; an inclined outer peripheral surface portion which is formed continuously with the first flat outer peripheral surface portion, an outer peripheral surface of the inclined outer peripheral surface portion having a diameter thereof gradually narrowed in a tapered shape in a direction toward the rear side from the first flat outer peripheral surface portion; and a second flat outer peripheral surface portion which is formed continuously with the inclined outer peripheral surface portion, an outer diameter of an outer peripheral surface of the second flat outer peripheral surface portion being fixed in the axial direction, wherein the ferrule includes, on an inner peripheral surface of the cylindrical portion thereof: a first flat inner peripheral surface portion which corresponds to the first flat outer peripheral surface portion of the second cylindrical body portion and has an inner diameter of an inner peripheral surface thereof set to a fixed value in the axial direction; an inclined inner peripheral surface portion which corresponds to the inclined outer peripheral surface portion of the second cylindrical body portion; and a second flat inner peripheral surface portion which corresponds to the second flat outer peripheral surface portion of the second cylindrical body portion and has an inner diameter of an inner peripheral surface thereof set to a fixed value in the axial direction, wherein assuming an inclination angle of the inclined outer peripheral surface portion as $\theta 1$ and an inclination angle of the inclined inner peripheral surface portion as $\theta 2$, the inclined angle $\theta 2$ of the inclined inner peripheral surface portion is set to a value which falls within a range of $0 \leq \theta 2 \leq \theta 1$, and a stepped portion is formed on a boundary between the first flat inner peripheral surface portion and the inclined inner peripheral surface portion, and the stepped portion is formed such that an end portion of the stepped portion on an inclined inner peripheral surface portion side is positioned in the middle of the inclined outer peripheral surface portion of the connector portion when the ferrule is brought into a state where the ferrule is mounted on the connector portion such that the pawl plate portion of the ferrule is brought into contact with the flat surface portion of the first cylindrical body portion.

As described above, the end portion of the stepped portion on the inclined inner peripheral surface portion side is positioned in the middle of the inclined outer peripheral surface portion of the connector portion when the ferrule is brought into a state where the ferrule is mounted on the connector portion. Accordingly, even when a tensile force toward the rear side is applied to the artificial blood vessel, the artificial blood vessel is minimally removed toward the rear side due to the presence of the stepped portion and hence, the reliability in connection between the artificial blood vessel and the artificial-blood-vessel connector can be increased.

In this specification, the inclination angle of the inclined outer peripheral surface portion of the connector portion is an inclination angle with respect to an extension surface which is an extension of a first flat outer peripheral surface portion of the connector portion toward a rear side. The inclination angle of the inclined inner peripheral surface portion of the ferrule is an inclination angle with respect to an extension surface which is an extension of a second flat inner peripheral surface portion of the ferrule toward a front side.

[3] In the artificial-blood-vessel connector of the present invention, it is preferable that the nut have a pressing force applying portion which applies a pressing force for linearly sliding the ferrule toward the front side to the ferrule at the time of connecting the nut to the connector portion, and the ferrule have a pressing force receiving portion which receives the pressing force of the nut, and the ferrule be configured to perform an operation where the ferrule is made to linearly slide toward the front side by receiving the pressing force of the nut so that the end portion of the stepped portion on the inclined inner peripheral surface portion side is made to slide along the inclined outer peripheral surface portion of the connector portion while pressing the artificial blood vessel.

In this manner, the ferrule performs the operation where, upon receiving a pressing force of the nut, the end portion of the stepped portion on the inclined inner peripheral surface portion side slides along the inclined outer peripheral surface portion of the connector portion while pressing the artificial blood vessel. Due to such an operation, in the artificial blood vessel, a raised portion is formed on a front side of the stepped portion. Since the raised portion performs a role of a removal stopper, even when a tensile force toward the rear side is applied to the artificial blood vessel, it is possible to surely prevent the artificial blood vessel from being removed from the connector portion and hence, the reliability in connection between the artificial blood vessel and the artificial-blood-vessel connector can be further increased.

[4] In the artificial-blood-vessel connector of the present invention, it is preferable that the pressing force applying portion which the nut has be an inner extending portion which is formed on a rear-side end portion of the nut in a circumferential direction such that the inner extending portion projects in a radially inward direction, and the pressing force receiving portion which the ferrule has be a notched portion formed on a rear-side end portion of the cylindrical portion of the ferrule along the circumferential direction, and be configured to bring the inner extending portion into contact with the notched portion.

By providing the nut and the ferrule with such a structure, it is possible to slide the ferrule toward a front side along with fastening of the nut.

[5] In the artificial-blood-vessel connector of the present invention, it is preferable that the artificial-blood-vessel connector further include a connection ring connectable to the object to be connected, the connection ring having a female threaded portion on an inner peripheral surface thereof so as to connect the connector portion to the object to be connected by making the female threaded portion of the connection ring threadedly engage with a female threaded portion formed on an object-to-be-connected side.

With the provision of such a connection ring, the artificial blood vessel can be easily and surely connected to an object to be connected.

[6] In the artificial-blood-vessel connector of the present invention, it is preferable that the artificial-blood-vessel connector further include a bending preventing member which prevents sharp bending of the artificial blood vessel at a rear-side end portion of the nut.

With the provision of the bending preventing member, it is possible to prevent sharp bending of the artificial blood vessel at the rear-side end portion of the nut. As the bending preventing member, for example, a cylindrical cover body made of a material such as silicon rubber having flexibility can be exemplified.

[7] In the artificial-blood-vessel connector of the present invention, it is preferable that the artificial blood vessel be an artificial blood vessel formed of a woven fabric made of resin fibers.

The artificial blood vessel formed of a woven fabric made of resin fibers has a small thickness and is weak against rubbing and hence, there is a high possibility that the artificial blood vessel is damaged by a frictional force generated due to fastening the nut. Accordingly, the present invention can acquire particularly large advantageous effects by applying the artificial-blood-vessel connector of the present invention to such an artificial blood vessel.

[8] In the artificial-blood-vessel connector of the present invention, it is preferable that the object to be connected be a blood pump or a cannula.

With such a configuration, by using the artificial-blood-vessel connector of the present invention as an artificial-blood-vessel connector in connecting an artificial blood vessel to a blood pump or a cannula, it is possible to prevent a damage on an artificial blood vessel formed of a woven fabric made of resin fibers and, at the same time, it is possible to increase reliability in connection between the artificial blood vessel and the artificial-blood-vessel connector.

[9] An artificial-blood-vessel unit of the present invention includes: an artificial blood vessel formed of a woven fabric made of resin fibers; and an artificial-blood-vessel connector for connecting the artificial blood vessel to an object to be connected, the artificial-blood-vessel connector being mounted on the artificial blood vessel, wherein the artificial-blood-vessel connector is the artificial-blood-vessel connector according to any one of the above-mentioned [1] to [8].

According to the artificial-blood-vessel unit of the present invention, as the artificial-blood-vessel connector, the artificial-blood-vessel connector described in any one of [1] to [8] is mounted on the artificial blood vessel. Accordingly, the artificial blood vessel which forms the artificial-blood-vessel unit can be a high-quality artificial blood vessel having no damage and, further, it is possible to provide an artificial-blood-vessel unit having high reliability in connection between the artificial blood vessel and the artificial-blood-vessel connector.

BRIEF DESCRIPTION OF DRAWINGS

FIG. 5A to FIG. 5D are views showing a nut 400 out of the respective members which form the artificial-blood-vessel connector 10A according to the embodiment 1.

DESCRIPTION OF EMBODIMENTS

Embodiments of the present invention are described hereinafter.

Embodiment 1

Figure 1A:
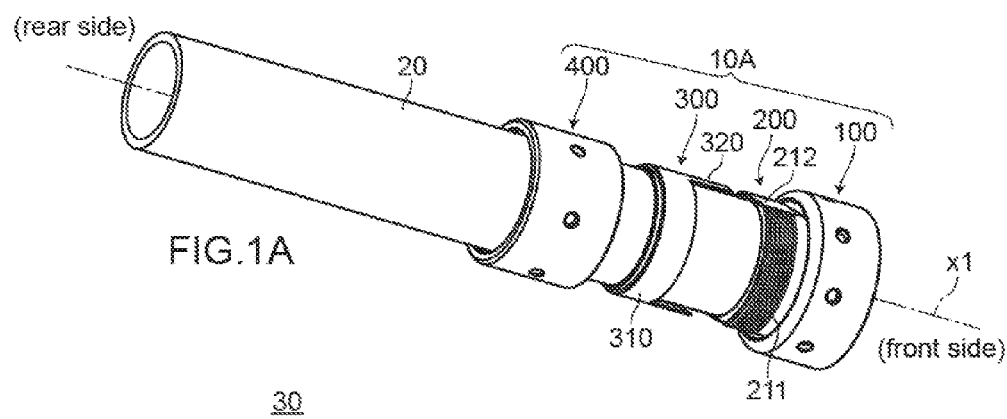
FIG. 1A and FIG. 1B are views for describing an artificial-blood-vessel connector 10A according to an embodiment 1.
Figure 1B:
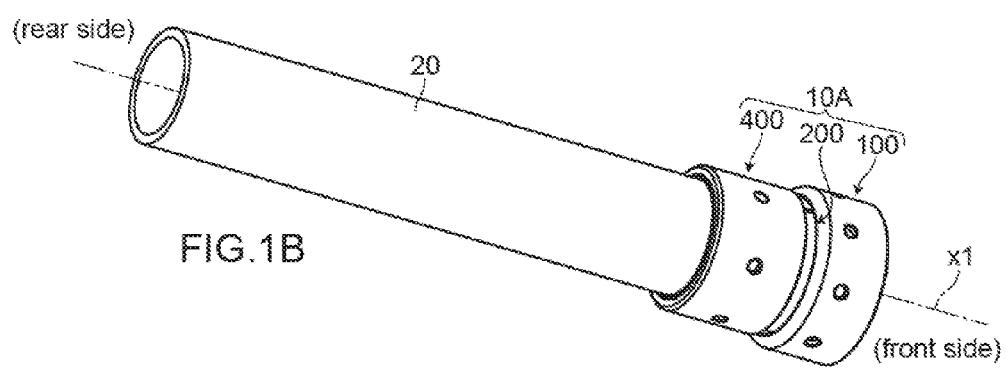

FIG. 1A and FIG. 1B are views for describing an artificial-blood-vessel connector 10A according to an embodiment 1. FIG. 1A shows a state before respective members which form the artificial-blood-vessel connector 10A according to the embodiment 1 are mounted on an artificial blood vessel 20 and the respective members are connected to each other. FIG. 1B shows a state where the respective members which form the artificial-blood-vessel connector 10A are mounted on the artificial blood vessel 20 and the respective members are mutually connected to each other. A unit in the state shown in FIG. 1B is referred to as "artificial-blood-vessel unit 30 according to the embodiment 1" or is simply referred to as "artificial-blood-vessel unit 30". In this embodiment 1, assume that an object to be connected to which the artificial blood vessel 20 is connected is a blood pump. Accordingly, in the embodiment 1, the description is made by assuming a side of the artificial blood vessel 20 which faces a blood pump as a front side, a side of the artificial blood vessel 20 opposite to the front side as a rear side, and a direction along a center axis X1 of the artificial blood vessel as an axial direction.

Figure 2A:
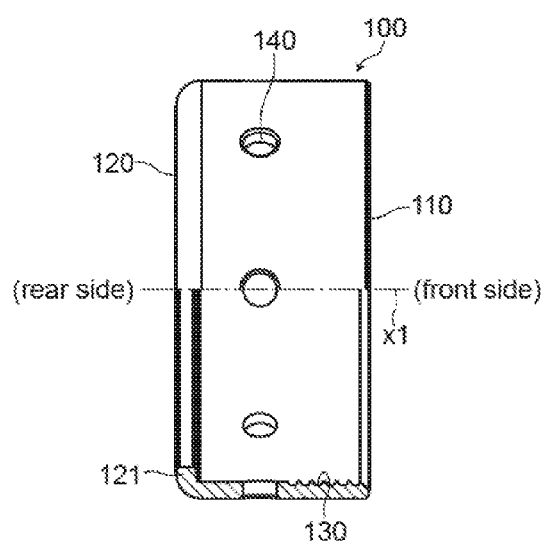
FIG. 2A and FIG. 2B are views for describing a connection ring out of respective members which form the artificial-blood-vessel connector 10A according to the embodiment 1.
Figure 2B:
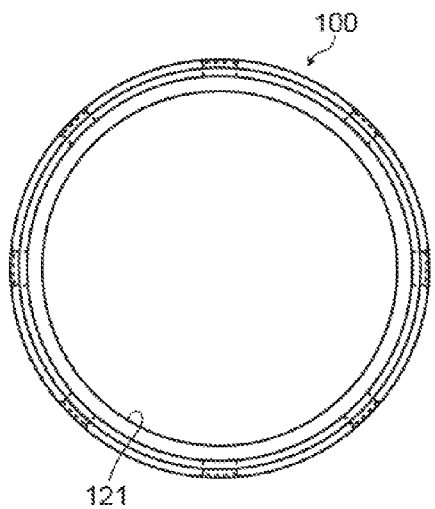

FIG. 2A and FIG. 2B are views for describing a connection ring 100 out of the respective members which form the artificial-blood-vessel connector 10A according to the embodiment 1. FIG. 2A and FIG. 2B are views showing a state where the connection ring 100 is removed from the artificial blood vessel 20. FIG. 2A is a side view of the connection ring 100, and FIG. 2B is a front view of the connection ring 100 as viewed toward the rear side from the front side.

Figure 3A:
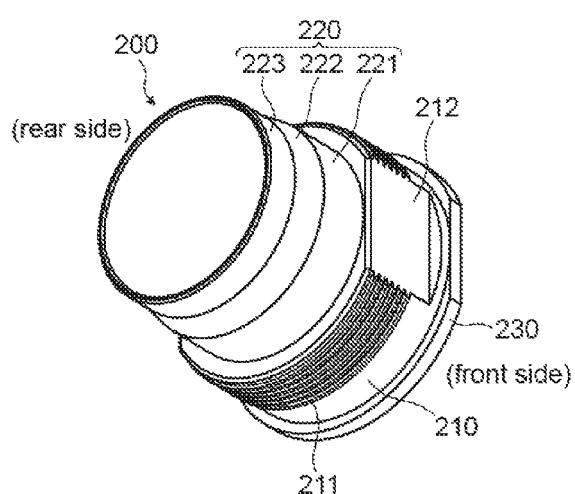
FIG. 3A to FIG. 3D are views showing a connector portion 200 out of the respective members which form the artificial-blood-vessel connector 10A according to the embodiment 1.
Figure 3B:
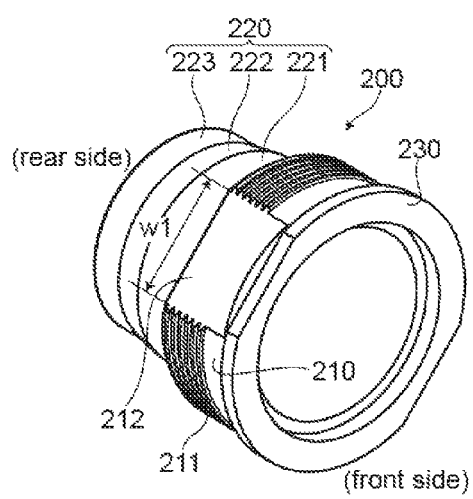
Figure 3C:
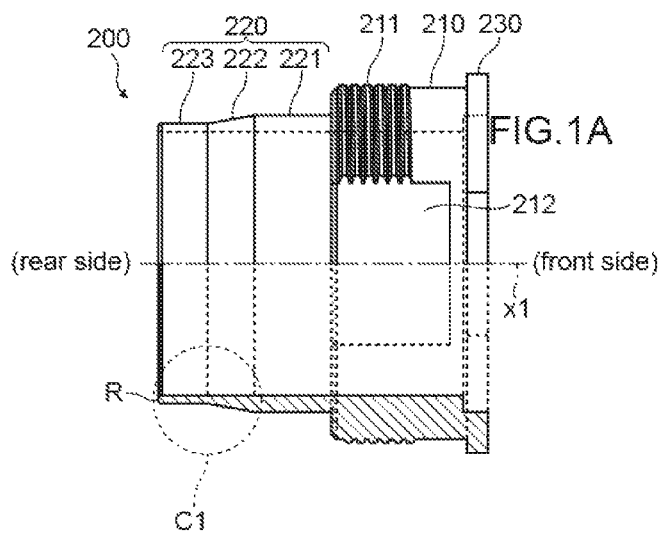
Figure 3D:
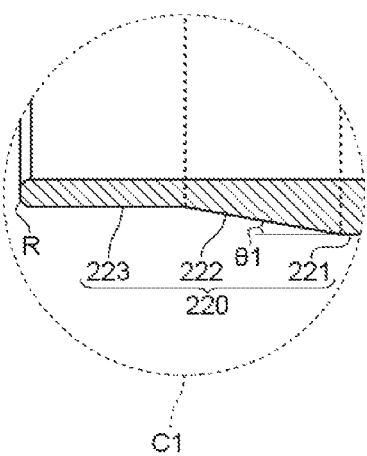

FIG. 3A to FIG. 3D are views showing a connector portion 200 out of the respective members which form the artificial-blood-vessel connector 10A according to the embodiment 1. FIG. 3A to FIG. 3D show a state where the connector portion 200 is removed from the artificial blood vessel 20. FIG. 3A is a perspective view of the connector portion 200 as viewed from an oblique rear side, FIG. 3B is a perspective view of the connector portion 200 as viewed from an oblique front side, FIG. 3C is a partial cross-sectional view taken along an axial direction of the connector portion 200, and FIG. 3D is an enlarged view in a circle C1 indicated by a broken line C1 shown in FIG. 3C.

Figure 4A:
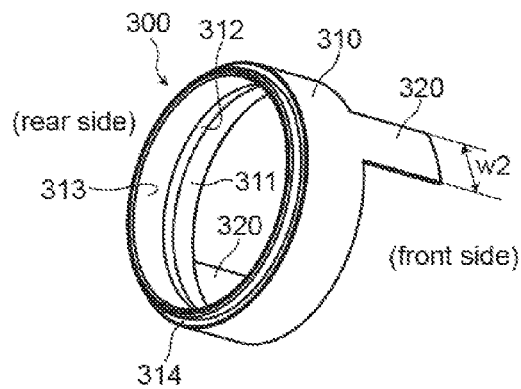
FIG. 4A to FIG. 4D are views showing a ferrule 300 out of the respective members which form the artificial-blood-vessel connector 10A according to the embodiment 1.
Figure 4B:
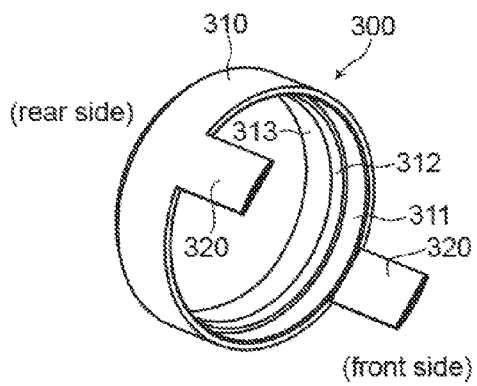
Figure 4C:
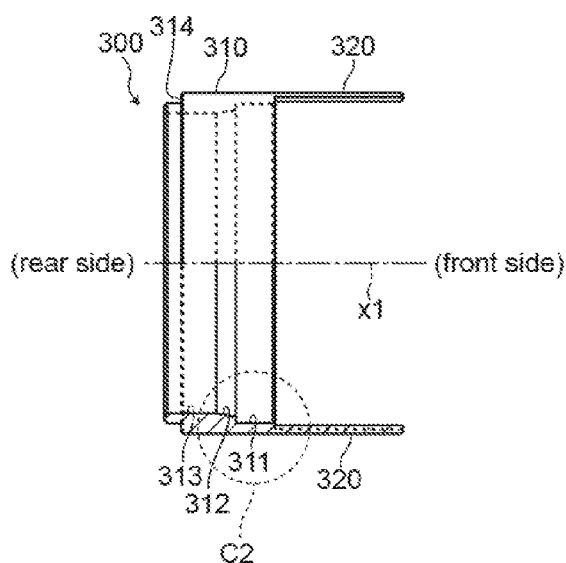
Figure 4D:
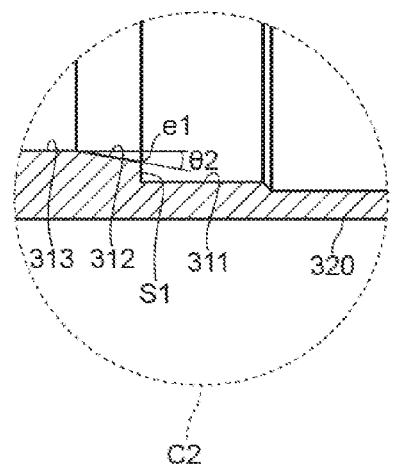

FIG. 4A to FIG. 4D are views showing a ferrule 300 out of the respective members which form the artificial-blood-vessel connector 10A according to the embodiment 1. FIG. 4A to FIG. 4D show a state where the ferrule 300 is removed from the artificial blood vessel 20. FIG. 4A is a perspective view of the ferrule 300 as viewed from an oblique rear side, FIG. 4B is a perspective view of the ferrule 300 as viewed from an oblique front side, FIG. 4C is a partial cross-sectional view along an axial direction of the ferrule 300, and FIG. 4D is an enlarged view in a circle C2 indicated by a broken line shown in FIG. 4C.

FIG. 5A to FIG. 5D are views showing a nut 400 out of the respective members which form the artificial-blood-vessel connector 10A according to the embodiment 1. FIG. 5A to FIG. 5D show a state where the nut 400 is removed from the artificial blood vessel 20. FIG. 5A is a perspective view of the nut 400 as viewed from an oblique rear side, FIG. 5B is a perspective view of the nut 400 as viewed from an oblique front side, FIG. 5C is a partial cross-sectional view along an axial direction of the nut 400, and FIG. 5D is an enlarged view in a circle C3 indicated by a broken line shown in FIG. 5C.

The artificial-blood-vessel connector 10A according to the embodiment 1 is described hereinafter.

As shown in FIG. 1A to FIG. 5D, the artificial-blood-vessel connector 10A according to the embodiment 1 includes: the connection ring 100 for connecting the artificial-blood-vessel connector 10A to a blood pump (not shown in FIG. 1A and FIG. 1B); the connector portion 200 having a first cylindrical body portion 210 and a second cylindrical body portion 220; the ferrule 300 having a cylindrical portion 310 and two pawl plate portions 320 formed in a projecting manner toward a front side from the cylindrical portion 310 along the axial direction; and the nut 400 connected to the connector portion 200 such that the nut 400 covers the ferrule 300.

The artificial blood vessel 20 is formed of a woven fabric made of resin fibers such as polyester and has a small thickness of approximately 0.2 mm. The artificial blood vessel 20 is configured such that a front-side end portion of the artificial blood vessel 20 is connected to a blood outflow port of a blood pump by the artificial-blood-vessel connector 10A according to the embodiment 1, and a rear-side end portion of the artificial blood vessel 20 is connected to a main artery by seaming, for example.

Hereinafter, the respective members (the connection ring 100, the connector portion 200, the ferrule 300 and the nut 400) which form the artificial-blood-vessel connector 10A according to the embodiment 1 are described individually.

First, as shown in FIG. 2A and FIG. 2B, the connection ring 100 has a cylindrical shape where a front-side end portion 110 and a rear-side end portion 120 are open-ended.

An inner extending portion 121 which extends inward along the radial direction is formed on the rear-side end portion 120 along the whole circumference in the circumferential direction. The inner extending portion 121 also plays a role of an engaging portion which is engageable with the connector portion 200.

On an inner peripheral surface of the connection ring 100, a female threaded portion 130 is formed within a predetermined range extending toward the rear-side end portion 120 from the front-side end portion 110. The female threaded portion 130 is formed so as to be threadedly engaged with a male threaded portion formed on a connecting fitting on a blood pump side (not shown in the drawing) at the time of connecting the connection ring 100 to the blood pump or the like, for example.

A plurality of through holes 140 are formed in the connection ring 100 in the vicinity of a center portion in the axial direction at predetermined intervals along a circumferential direction. The through holes 140 are formed so as to allow the insertion of a fastening pin or the like thereinto at the time of fastening the connection ring 100 by making the connection ring 100 threadedly engage with the male threaded portion formed on the connecting fitting on a blood pump side, for example.

Next, the connector portion 200 is described.

As shown in FIG. 3A to FIG. 3D, the connector portion 200 includes the first cylindrical body portion 210 and the second cylindrical body portion 220. A male threaded portion 211 and a flat surface portion 212 on which the male threaded portion 211 is not formed are alternately formed on an outer peripheral surface of the first cylindrical body portion 210 along a circumferential direction. The second cylindrical body portion 220 is continuously formed with a rear side of the first cylindrical body portion 210. The second cylindrical body portion 220 has an outer diameter smaller than that of the first cylindrical body portion 210, and the second cylindrical body portion 220 is insertable into the inside of the artificial blood vessel 20.

A flange portion 230 which projects radially outward is formed on a front-side end portion of the connector portion 200. The flange portion 230 engages with the inner extending portion 121 formed on the rear-side end portion 120 of the connection ring 100.

The second cylindrical body portion 220 is formed of: a first flat outer peripheral surface portion 221 where an outer diameter of an outer peripheral surface is set to a fixed value in the axial direction; an inclined outer peripheral surface portion 222 which is formed continuously with the first flat outer peripheral surface portion 221, and has a tapered outer peripheral surface whose diameter is gradually decreased toward a rear side from the first flat outer peripheral surface portion 221; and a second flat outer peripheral surface portion 223 which is formed continuously with the inclined outer peripheral surface portion 222, and has an outer diameter of an outer peripheral surface thereof fixed in the axial direction. The outer diameter of the second flat outer peripheral surface portion 223 is set to a value which is equal to an inner diameter of the artificial blood vessel 20 or a value which is slightly larger than the inner diameter of the artificial blood vessel 20.

A round R is formed on a rear-side end portion of the second cylindrical body portion 220 (a rear-side end portion of the second flat outer peripheral surface portion 223). In this manner, the round R is formed on the rear-side end portion of the second cylindrical body portion 220 and hence, it is possible to acquire an advantageous effect that a blood which flows through the second cylindrical body portion 220 minimally hemolyzes.

An inclination angle θ1 of the inclined outer peripheral surface portion 222 is set to approximately 10 degrees. Assume that the inclination angle θ1 of the inclined outer peripheral surface portion 222 in the connector portion 200 is an inclination angle with respect to an extension surface which is an extension of the first flat outer peripheral surface portion 221 toward a rear side. An inner peripheral surface of the first cylindrical body portion 210 and an inner peripheral surface of the second cylindrical body portion 220 forma flat smooth surface where neither a stepped portion nor a joint is formed. Although the inclination angle θ1 is set to approximately 10 degrees in this case, the inclination angle θ1 is not limited to such a value.

As described previously, on the outer peripheral surface of the first cylindrical body portion 210 of the connector portion 200, the male threaded portion 211 and the flat surface portion 212 on which the male threaded portion 211 is not formed are alternately formed along the circumferential direction of the outer peripheral surface. The male threaded portion 211 is formed within a range from a rear-side end portion to an approximately middle portion toward a front-side end portion of the first cylindrical body portion 210. The flat surface portion 212 is formed at two positions on the outer peripheral surface of the first cylindrical body portion 210. It is preferable that the respective flat surface portions 212 be formed at positions on sides opposite to each other with a center axis X1 sandwiched therebetween. The flat surface portion 212 is formed of a flat-surface recessed portion which is lower than the male threaded portion by one step.

The respective flat surface portions 212 are formed within a range from a rear-side end portion of the first cylindrical body portion 210 to the flange portion 230 in the axial direction. A width (width in a circumferential direction) W1 of each flat surface portion 212 is set approximately equal to or slightly larger than a width W2 of two pawl plate portions 320 of the ferrule 300 described later (see FIG. 4A to FIG. 4D).

Next, the ferrule 300 is described.

As shown in FIG. 3A to FIG. 3D, the ferrule 300 includes: the cylindrical portion 310 which can be fitted on the connector portion 200 by way of the artificial blood vessel 20 when the second cylindrical body portion 220 of the connector portion 200 is fitted in the artificial blood vessel 20; and the pawl plate portions 320 which are formed in a projecting manner from the cylindrical portion 310 in the axial direction, and are brought into contact with the flat surface portions 212 of the first cylindrical body portion 210.

On an inner peripheral surface of the cylindrical portion 310, a first flat inner peripheral surface portion 311, an inclined inner peripheral surface portion 312 and a second flat inner peripheral surface portion 313 are formed. The first flat inner peripheral surface portion 311 corresponds to the first flat outer peripheral surface portion 221 of the connector portion 200, and an inner diameter of an inner peripheral surface of the first flat inner peripheral surface portion 311 is set to a fixed value in the axial direction. The inclined inner peripheral surface portion 312 corresponds to the inclined outer peripheral surface portion 222 of the connector portion 200. The second flat inner peripheral surface portion 313 corresponds to the second flat outer peripheral surface portion 223 of the connector portion 200, and an inner diameter of an inner peripheral surface of the second flat inner peripheral surface portion 313 is set to a fixed value in the axial direction.

The inclined inner peripheral surface portion 312 has a tapered shape whose diameter is gradually increased in a direction toward the front side from the second flat inner peripheral surface portion 313, and an inclination angle of the inclined inner peripheral surface portion 312 is set to θ2. Assume that the inclination angle θ2 of the inclined inner peripheral surface portion 312 of the ferrule is an inclination angle with respect to an extension surface which is an extension of the second flat inner peripheral surface portion 313 toward the front side. Further, in the embodiment 1, the inclination angle θ2 of the inclined inner peripheral surface portion 312 is equal to the inclination angle θ1 of the inclined outer peripheral surface portion 222 of the connector portion 200.

A stepped portion S1 is formed on a boundary between the first flat inner peripheral surface portion 311 and the inclined inner peripheral surface portion 312. The stepped portion S1 is formed such that an end portion e1 of the stepped portion S1 on an inclined inner peripheral surface portion 312 side (hereinafter also abbreviated as the end portion e1 of the stepped portion S1) is positioned in the middle of the inclined outer peripheral surface portion 222 of the second cylindrical body portion 220 in a state where the ferrule 300 is mounted on the connector portion 200.

Further, a notched portion 314 having an L-shaped cross section is formed on a rear-side end portion of the cylindrical portion 310 along the whole circumference in a circumferential direction. The notched portion 314 functions as a pressing force receiving portion which receives a pressing force of the nut 400.

Two pawl plate portions 320 are formed on the cylindrical portion 310 such that two pawl plate portions 320 face each other in a diametrical direction. In a state where the ferrule 300 is mounted on the connector portion 200, the respective pawl plate portions 320 are brought into contact with the flat surface portions 212 of the first cylindrical body portion 210 which correspond to the respective pawl plate portions 320 and hence, the ferrule 300 is not rotated even when a rotational force in a circumferential direction is applied to the ferrule 300.

Further, an inner diameter of the first flat inner peripheral surface portion 311 is set slightly larger than an outer diameter of the first flat outer peripheral surface portion 221 of the second cylindrical body portion 220, and an inner diameter of the second flat inner peripheral surface portion 313 is set slightly larger than an outer diameter of the second flat outer peripheral surface portion 223 of the second cylindrical body portion 220. A distance in a diametrical direction between two pawl plate portions 320 is set slightly larger than an inner dimer of the first flat inner peripheral surface portion 311.

With such a configuration, in mounting the ferrule 300 on the connector portion 200 in a state where the second cylindrical body portion 220 is fitted in the artificial blood vessel 20, the ferrule 300 can be mounted on the connector portion 200 in a state where the connector portion 200 is fitted in the artificial blood vessel 20 by making the ferrule 300 slide linearly along the axial direction without rotating the ferrule 300 in a circumferential direction (without making the ferrule 300 threadedly engage with the connector portion 200). Further, in mounting the ferrule 300 on the connector portion 200, the ferrule 300 is made to slide linearly in a state where the respective pawl plate portions 320 and the flat surface portions 212 of the first cylindrical body portion 210 which respectively correspond to the pawl plate portions 320 are positioned to be aligned on the same straight line.

When the ferrule 300 is mounted on the connector portion 200 in this manner, the first flat inner peripheral surface portion 311 is brought into a state where the first flat inner peripheral surface portion 311 substantially faces the first flat outer peripheral surface portion 221 of the second cylindrical body portion 220 with the artificial blood vessel interposed therebetween, and the second flat inner peripheral surface portion 313 is brought into a state where the second flat inner peripheral surface portion 313 substantially faces the second flat outer peripheral surface portion 223 of the second cylindrical body portion 220 with the artificial blood vessel 20 interposed therebetween.

Father, the inclined inner peripheral surface portion 312 is brought into a state where the inclined inner peripheral surface portion 312 substantially faces the inclined outer peripheral surface portion 222 of the connector portion 200 with the artificial blood vessel 20 interposed therebetween. In such a state, the stepped portion S1 is positioned on the boundary between the first flat inner peripheral surface portion 311 and the inclined inner peripheral surface portion 312. To be more specific, the end portion e1 of the stepped portion S1 is positioned in the middle of the inclined outer peripheral surface portion 222 of the connector portion 200. The ferrule 300 which is mounted on the connector portion 200 in this manner is further slidable toward the front side by a slight amount. This operation is described later.

Next, the nut 400 is described.

As shown in FIG. 5A to FIG. 5D, a female threaded portion 410 which is configured to threadedly engage with the male threaded portion 211 of the first cylindrical body portion 210 of the connector portion 200 is formed on the inner peripheral surface of the nut 400. A plurality of through holes 420 are formed in the vicinity of a center portion of the nut 400 in the axial direction such that the plurality of through holes 420 are arranged at predetermined intervals along a circumferential direction. The through holes 420 are formed so as to allow the insertion of a fastening pin or the like thereinto at the time of fastening the nut 400 by making the female threaded portion 410 of the nut 400 threadedly engage with the male threaded portion 211 formed on the connector portion 200.

An inner extending portion 430 which slightly extends toward the inside in a radial direction is formed on a rear-side end portion of the nut 400 such that the inner extending portion 430 is formed along the whole circumference in a circumferential direction. The inner extending portion 430 is configured to be brought into contact with the notched portion 314 formed on the cylindrical portion 310 of the ferrule 300. The inner extending portion 430 functions as a pressing force applying portion for applying a pressing force to the ferrule 300.

With respect to the nut 400 having such a configuration, in a state where the second cylindrical body portion 220 of the connector portion 200 is fitted in the artificial blood vessel 20 and the ferrule 300 is mounted on the connector portion 200, the nut 400 can be connected to the connector portion 200 by making the female threaded portion 410 threadedly engage with the male threaded portion 211 of the first cylindrical body portion 210 such that the nut 400 covers the ferrule 300.

The above-mentioned respective members which form the artificial-blood-vessel connector 10A (the connection ring 100, the connector portion 200, the ferrule 300 and the nut 400) are made of pure titanium which is a material having excellent blood compatibility. It is also possible to use a titanium alloy (preferably Ti-6Al-4V alloy) in place of pure titanium.

The steps of mounting the artificial-blood-vessel connector 10A according to this embodiment 1 to the artificial blood vessel 20 is described hereafter. First, a state is brought about where the nut 400 is fitted on the artificial blood vessel 20, and the ferrule 300 is fitted on the artificial blood vessel 20. Both the connector portion 200 and the connection ring 100 are connected to each other such that the flange portion 230 of the connector portion 200 engages with the inner extending portion 121 of the connection ring 100.

Then, the second cylindrical body portion 220 of the connector portion 200 is fitted in the artificial blood vessel 20 in a state where the nut 400 and the ferrule 300 are fitted on the artificial blood vessel 20. Then, the ferrule 300 is mounted on the connector portion 200 by making the ferrule 300 linearly slide along the axial direction such that two pawl plate portions 320 of the ferrule 300 are brought into contact with the flat surface portions 212 of the first cylindrical body portion 210 of the connector portion 200 which correspond to two pawl plate portions 320 respectively and, thereafter, the nut 400 is fastened by making the female threaded portion 410 of the nut 400 threadedly engage with the male threaded portion 211 of the first cylindrical portion 210 of the connector portion 200.

Through such steps, the artificial-blood-vessel connector 10A according to the embodiment 1 can be mounted on the artificial blood vessel 20 (see FIG. 1B). In fastening the nut 400, the nut 400 can be surely connected to the connector portion 200 by performing the fastening while inserting a fastening pin or the like into the insertion hole 420.

In this manner, in fastening the nut 400, the nut 400 is fastened by rotating the nut 400 in a state where the nut 400 is not brought into direct contact with the artificial blood vessel 20 due to the presence of the ferrule 300. Accordingly, there is no possibility that a frictional force generated by rotation of the nut 400 is applied to the artificial blood vessel 20 so that it is possible to surely prevent the occurrence of a drawback that the artificial blood vessel is rubbed by a frictional force due to fastening the nut so that the artificial blood vessel is damaged.

In fastening the nut 400 by making the female threaded portion 410 of the nut 400 threadedly engage with the male threaded portion 211 of the first cylindrical body portion 210 of the connector portion 200, the nut 400 is fastened in a state where the inner extending portion 430 formed on the rear-side end portion of the nut 400 is brought into contact with the notched portion 314 formed in the rear-side end portion of the ferrule 300.

Accordingly, when the nut 400 is fastened, the pressing force in a direction toward the front side from the rear side is applied to the ferrule 300. Accordingly, the ferrule 300 is made to slightly slide linearly toward the front side along the axial direction. Due to such slight linear sliding of the ferrule 300 toward the front side, the inclined inner peripheral surface portion 312 of the ferrule 300 is made to slightly slide toward the front side along the inclined outer peripheral surface portion 222 of the connector portion 200 while pressing the inclined outer peripheral surface portion 222 of the connector portion 200 by way of the artificial blood vessel 20. Along with such an operation, the stepped portion S1 formed at the boundary between the first flat inner peripheral surface portion 311 and the inclined inner peripheral surface portion 312 of the ferrule 300 performs a slight sliding operation along the inclined outer peripheral surface portion 222 of the connector portion 200.

Figure 6A:
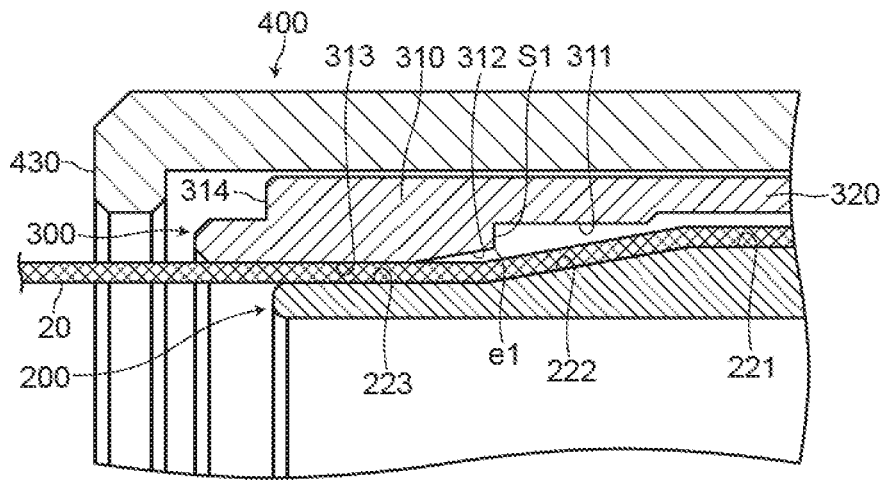
FIG. 6A and FIG. 6B are views for describing an operation of the ferrule 300 caused by fastening the nut 400.
Figure 6B:
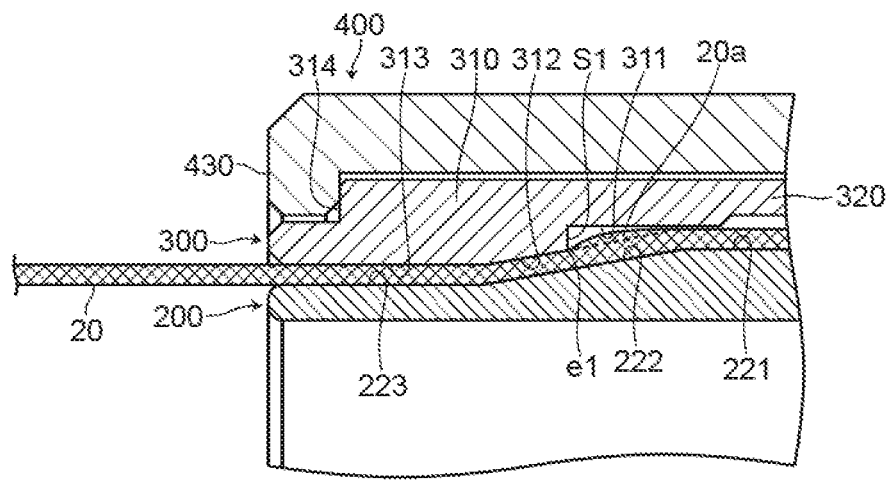

FIG. 6A and FIG. 6B are views for describing an operation of the ferrule 300 caused by fastening the nut. FIG. 6A and FIG. 6B are schematic partial cross-sectional views taken along the axial direction showing a state where the ferrule 300 and the nut 400 are mounted on the connector portion 200 with the artificial blood vessel 20 interposed therebetween. FIG. 6A shows a state before a nut fastening operation is started, and FIG. 6B shows a state after the nut fastening operation is finished.

In FIG. 6A and FIG. 6B, constitutional elements identical with the constitutional elements shown in FIG. 1A to FIG. 5D are given same symbols. However, FIG. 6A and FIG. 6B are schematic views and hence, some constitutional elements are described in an exaggerated manner and some other constitutional elements are omitted from the drawings.

The operation of the ferrule 300 caused by fastening the nut 400 is described with reference to FIG. 6A and FIG. 6B. First, when the nut 400 is fastened by rotating the nut 400 in a clockwise direction from the state shown in FIG. 6A, the nut 400 advances toward the front side along with the rotation thereof so that the inner extending portion 430 formed on the rear-side end portion of the nut 400 is brought into contact with the notched portion 314 formed on the rear-side end portion of the cylindrical portion 310 of the ferrule 300 and presses the ferrule 300 toward the front side.

With such a configuration, the ferrule 300 is made to slightly slide linearly toward the front side. Due to such slight linear sliding of the ferrule 300 toward the front side along the axial direction, the inclined inner peripheral surface portion 312 of the ferrule 300 is made to slightly slide toward the front side along the inclined outer peripheral surface portion 222 of the connector portion 200 while pressing the inclined outer peripheral surface portion 222 of the connector portion 200 by way of the artificial blood vessel 20. Along with such an operation, the stepped portion S1 formed on the ferrule 300 also performs the slight sliding operation along the inclined outer peripheral surface portion 222 of the connector portion 200. In the operation where the stepped portion S1 of the ferrule 300 performs the slight sliding operation along the inclined outer peripheral surface portion 222 of the connector portion 200, the end portion e1 of the stepped portion S1 performs the slight sliding operation along the inclined outer peripheral surface portion 222 of the connector potion 200 while pressing the artificial blood vessel 20.

When the end portion e1 of the stepped portion S1 performs the slight sliding operation along the inclined outer peripheral surface portion 222 of the connector portion 200 while pressing the artificial blood vessel 20, as shown in FIG. 6B, in the artificial blood vessel 20, a raised portion 20a is formed on the front side of the stepped portion S1. This raised portion 20a may be referred to as a wrinkle generated by pressing the artificial blood vessel 20 toward the front side by the end portion e1 of the stepped portion S1. Since the artificial blood vessel 20 is pressed toward the front side by the end portion e1 of the stepped portion S1, the wrinkle is minimally generated on the artificial blood vessel 20 on the rear side of the end portion e1 of the stepped portion S1.

As shown in FIG. 6B, when the artificial blood vessel 20 is brought into a state where the raised portion 20a is formed on the front side of the stepped portion S1, the raised portion 20a performs a role of a removal stopper. Accordingly, even when a tensile force toward the rear side is applied to the artificial blood vessel 20, it is possible to surely prevent the artificial blood vessel 20 from being removed from the connector portion 200 and hence, the reliability in connection between the artificial blood vessel 20 and the artificial-blood-vessel connector 10A can be further increased.

Figure 7:
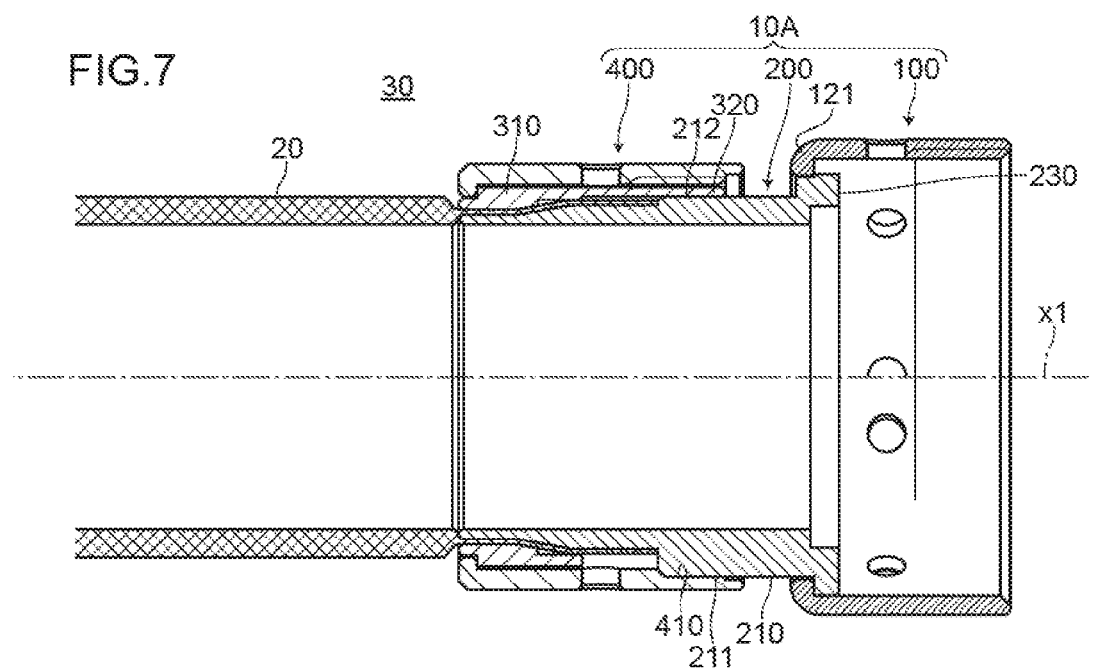
FIG. 7 is a cross-sectional view showing a state where the artificial-blood-vessel connector 10A according to the embodiment 1 is mounted on an artificial blood vessel 20.

FIG. 7 is a cross-sectional view showing a state where the artificial-blood-vessel connector 10A according to the embodiment 1 is mounted on the artificial blood vessel 20. FIG. 7 is also a cross-sectional view taken along an axial direction at an angle of 90 degrees with respect to a center axis X1 shown in FIG. 1B. Accordingly, in FIG. 7, a portion of the ferrule 300 where the pawl plate portion 320 is brought into contact with the flat surface portion 212 of the first cylindrical body portion 210 in the connector portion 200 is shown on a side above the center axis X1, and a portion of the ferrule 300 where the pawl plate portion 320 does not exist, that is, a portion where the flat surface portion 212 is not formed on the first cylindrical body portion 210 (a portion where the male threaded portion 211 of the first cylindrical body portion 210 is formed) is shown on a side below the center axis X1. Further, in FIG. 7, constitutional elements identical with the constitutional elements shown in FIG. 1A to FIG. 6B are given same symbols.

FIG. 7 shows a state where the connection ring 100 and the connector portion 200 engage with each other. The connection ring 100 and the connector portion 200 are connected to each other in a state where the inner extending portion 121 formed on the rear-side end portion 120 of the connection ring 100 engages with the flange portion 230 formed on the front-side end portion of the connector portion 200. The connection ring 100 is used for connecting the artificial-blood-vessel connector 10A to a connecting fitting of a blood pump or the like, for example. The connection structure between the connection ring 100 and the connector portion 200 is not the gist of the present invention and hence, the detailed description of the connection structure is omitted.

With respect to the connector portion 200, the second cylindrical body portion 220 of the connector portion 200 is fitted in the artificial blood vessel 20. The ferrule 300 is in a state where two pawl plate portions 320 are brought into contact with two flat surface portions 212 formed on the first cylindrical body portion 210 of the connector portion 200. In FIG. 7, however, out of two pawl plate portions 320 and two flat surface portions 212, only one pawl plate portion and one flat surface portion are viewable with naked eyes.

The cylindrical portion 310 of the ferrule 300 is fitted on the second cylindrical body portion 220 of the connector portion 200 with the artificial blood vessel 20 interposed therebetween (see FIG. 6A and FIG. 6B with respect to the detail of the configuration). The ferrule 300 is mounted on the connector portion 200 as described with reference to FIG. 6A and FIG. 6B by fastening the nut 400 in a state where the female threaded portion 410 of the nut 400 is threadedly engaged with the male threaded portion 211 of the connector portion 200.

The configuration in a state where the artificial-blood-vessel connector 10A according to the embodiment 1 is connected to the artificial blood vessel 20 (see FIG. 1B and FIG. 7) forms the artificial-blood-vessel unit 30 according to the embodiment 1. In connecting such an artificial-blood-vessel unit 30 to a blood outflow port of the blood pump, for example, the female threaded portion 130 formed on the inner peripheral surface of the connection ring 100 is threadedly engaged with the male threaded portion formed on the connecting fitting of the blood pump on a blood outflow port side (not shown in the drawing), and the connection ring 100 is fastened. In fastening the connection ring 100, by performing such fastening by inserting a fastening pin or the like into the through hole 140, the connection ring 100 can be surely connected to the connecting fitting on a blood pump side. When the connection ring 100 is connected to the connecting fitting on a blood pump side, the connector portion 200 is hermetically joined to the connecting fitting on a blood pump side in a state where an O ring (not shown in the drawing) or the like is interposed between the connector portion 200 and the connecting fitting.

Figure 8:
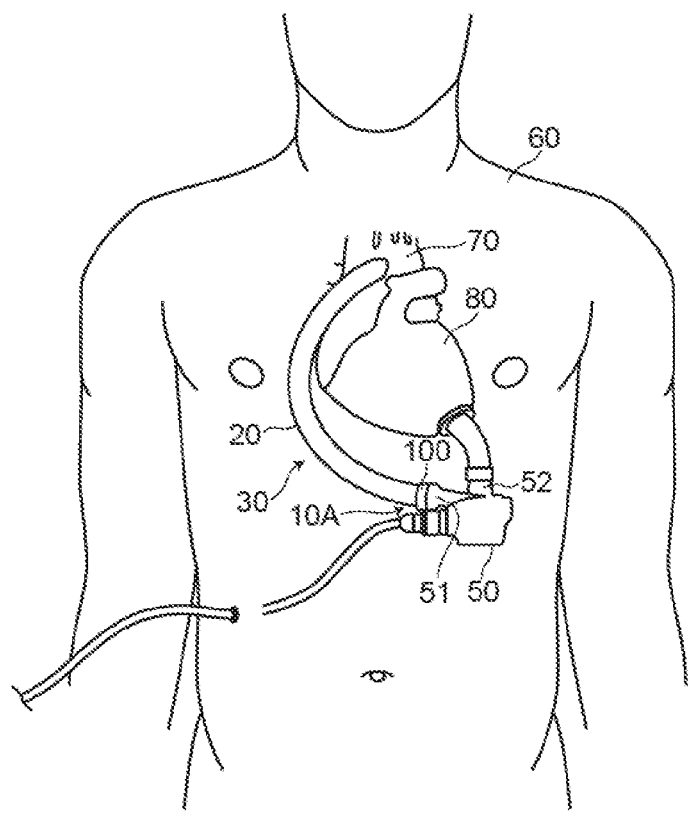
FIG. 8 is a view schematically showing a use example of an artificial-blood-vessel unit 30 according to the embodiment 1.

FIG. 8 is a view schematically showing a use example of the artificial-blood-vessel unit 30 according to the embodiment 1. In FIG. 8, the case is exemplified where the artificial-blood-vessel unit 30 according to the embodiment 1 is used for connecting the blood outflow port 51 of the blood pump 50 and a main artery 70 of a human body 60. In FIG. 8, an external controller for driving the blood pump 50, a helix wound around the artificial blood vessel and the like are omitted from the drawing.

As shown in FIG. 8, on one side of the artificial-blood-vessel unit 30 (a side where the artificial-blood-vessel connector 10A is present), the connection ring 100 of the artificial-blood-vessel connector 10A is connected to the connecting fitting (not shown in the drawing) of the blood outflow port 51 of the blood pump 50, while the other side of the artificial-blood-vessel unit 30 is connected to the main artery 70, for example, by seaming or the like.

In FIG. 8, the case is exemplified where the artificial-blood-vessel unit 30 according to the embodiment 1 connects the blood outflow port 51 of the blood pump 50 and the main artery 70 to each other. However, an artificial-blood-vessel unit having substantially the same structure as the artificial-blood-vessel unit 30 according to the embodiment 1 can be also used for connection between a left ventricle 80 of the human body 60 and the blood inflow port 52 of the blood pump 50.

As has been described heretofore, according to the artificial-blood-vessel connector 10A according to the embodiment 1, it is possible to prevent a damage on an artificial blood vessel formed of a woven fabric made of resin fibers and, at the same time, it is possible to increase reliability in connection between the artificial blood vessel and the artificial-blood-vessel connector 10A after these parts are connected to each other.

That is, in mounting the nut 400 on the connector portion 200, the nut 400 is fastened by making the female threaded portion 410 of the nut 400 threadedly engage with the male threaded portion 211 of the connector portion 200. In this nut fastening operation, it is possible to fasten the nut 400 in a state where the nut 400 is not brought into direct contact with the artificial blood vessel 20 due to the presence of the ferrule 300. Accordingly, there is no possibility that a frictional force generated by rotation of the nut 400 is applied to the artificial blood vessel 20 so that it is possible to surely prevent the occurrence of a drawback that the artificial blood vessel is rubbed by a frictional force due to fastening the nut so that the artificial blood vessel is damaged. As a result, it is possible to prevent a damage on the artificial blood vessel formed of a woven fabric made of resin fibers.

When the nut 400 is fastened, the ferrule 300 is pressed by the nut 400 and is made to slightly slide toward the front side. Accordingly, the artificial blood vessel 20 is brought into a state where the raised portion 20a is formed on the front side of the stepped portion S1, the raised portion 20a performs a role of a removal stopper so that the artificial blood vessel is minimally removed from the connector portion 200.

Accordingly, in the artificial-blood-vessel connector 10A according to the embodiment 1, even when the tensile force toward the rear side is applied to the artificial blood vessel 20, it is possible to surely prevent the artificial blood vessel 20 from being removed from the connector portion 200 and hence, the reliability in connection between the artificial blood vessel and the artificial-blood-vessel connector can be further increased.

Further, according to the artificial-blood-vessel unit of the embodiment 1, with the use of the artificial-blood-vessel connector 10A according to the embodiment 1 as the artificial-blood vessel connector, it is possible to provide the high-quality artificial blood vessel having no damages as the artificial blood vessel 20 which forms a part of the artificial-blood-vessel unit 40. Further, it is also possible to provide the artificial-blood-vessel unit which exhibits high reliability in connection between the artificial blood vessel 20 and the artificial-blood-vessel connector 10A.

The artificial-blood-vessel unit 30 according to the embodiment 1 has been described with respect to the case where the artificial blood vessel 20 is connected to the blood pump. However, the artificial-blood-vessel unit 30 according to the embodiment 1 can be also used in the case where the artificial blood vessel 20 is connected to a cannula (not shown in the drawing). When the artificial-blood-vessel unit 30 according to the embodiment 1 is used in the case where the artificial blood vessel 20 is connected to the cannula, a male threaded portion with which the female threaded portion 130 of the connection ring 100 can threadedly engage is formed on a cannula side. With such a configuration, the artificial-blood-vessel unit 30 according to the embodiment 1 can be connected to the cannula.

Although not shown in the FIG. 1B and FIG. 7, it is preferable that the artificial-blood-vessel connector 10A include a bending preventing member which prevents sharp bending of the artificial blood vessel 20 at the rear-side end portion of the nut 400.

Figure 9:
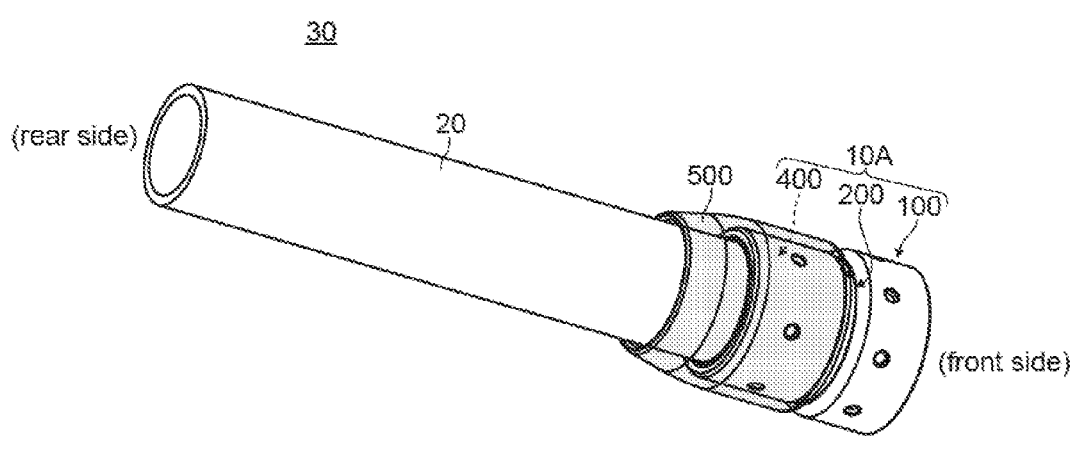
FIG. 9 is a view showing a case where a bending preventing member 500 is mounted on the nut 400 and an artificial blood vessel 20 of a predetermined range.

FIG. 9 is a view showing a case where a bending preventing member 500 is mounted on the nut 400 and a predetermined range of an artificial blood vessel 20. In FIG. 9, the case is exemplified where, for example, a cylindrical cover body having resiliency such as silicon rubber is used as the bending preventing member 500.

By mounting the bending preventing member 500 on the artificial-blood-vessel connector 10A such that the bending preventing member 500 covers the nut 400 and a predetermined range of the artificial blood vessel 20, for example, it is possible to prevent sharp bending of the artificial blood vessel 20 at the rear-side end portion of the nut 400. The range that the bending preventing member 500 covers may be set such that the bending preventing member 500 covers the whole nut 400 or the bending preventing member 500 covers a part of the end portion of the nut 400 on a nut side. Further, on an artificial blood vessel 20 side, when a helix (not shown in the drawing) is present in the artificial blood vessel 20, it is preferable that the bending preventing member 500 also covers a portion where the helix is present. The bending preventing member 500 is not limited to the bending preventing member 500 shown in FIG. 9.

Embodiment 2

Figure 10A:
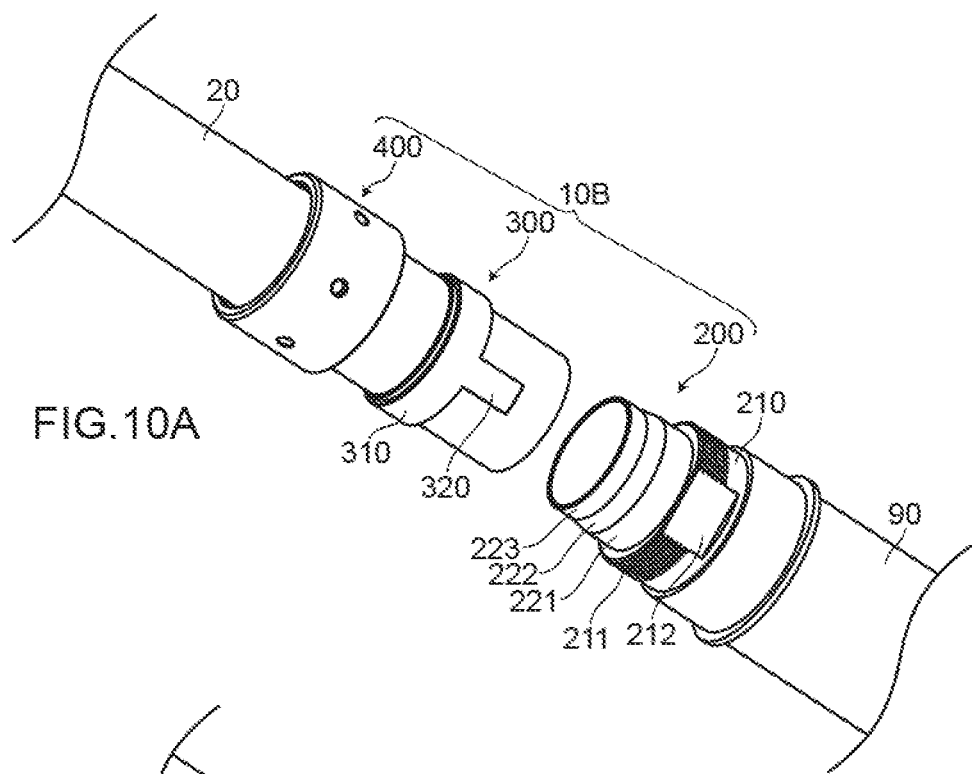
FIG. 10A and FIG. 10B are views for describing an artificial-blood-vessel connector 10B according to an embodiment 2.
Figure 10B:
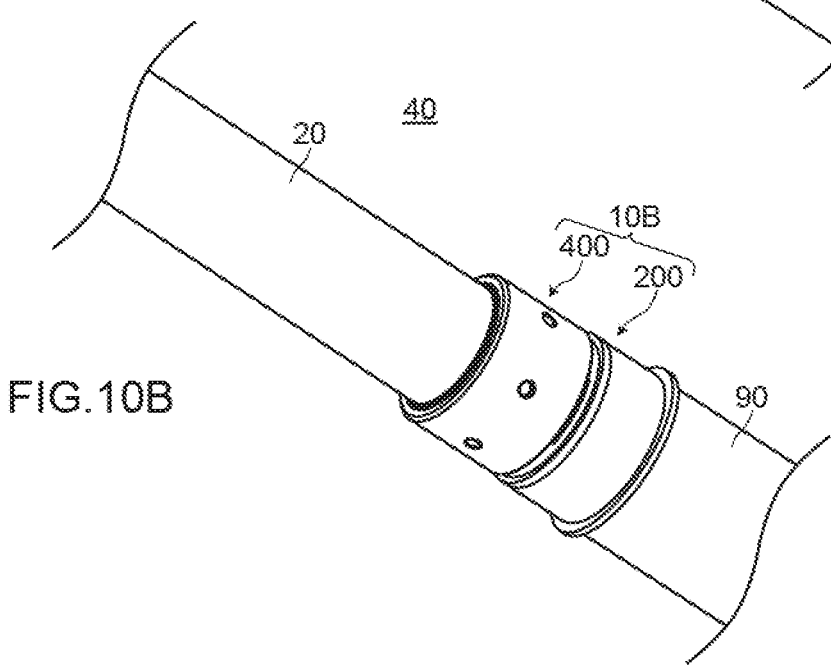
Figure 11:
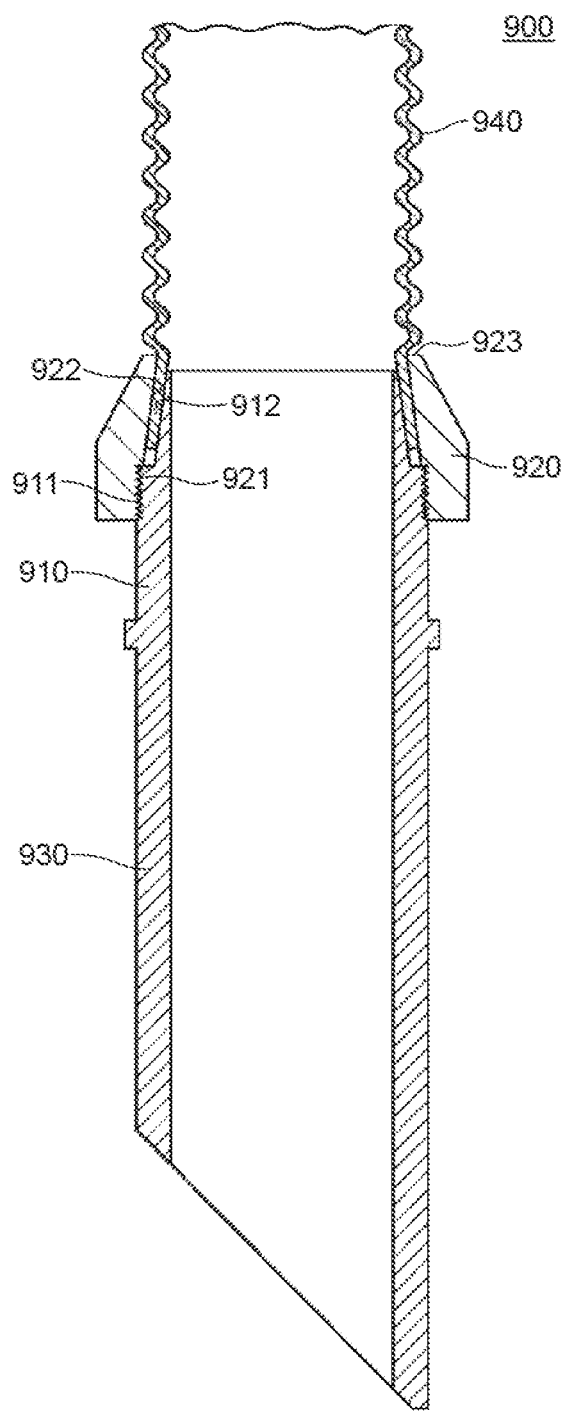
FIG. 11 is a view for describing an artificial-blood-vessel connector 900 described in patent literature 1.

FIG. 10A and FIG. 10B are views for describing an artificial-blood-vessel connector 10B according to an embodiment 2. FIG. 10A and FIG. 10B show the case where a connector portion 200 is provided on a side of an object to be connected to an artificial blood vessel 20. In this embodiment, the object to be connected to the artificial blood vessel 20 is a cannula 90.

FIG. 10A shows a state before respective members which form the artificial-blood-vessel connector 10B according to the embodiment 2 are mounted on the artificial blood vessel 20 and the respective members are mutually connected to each other. FIG. 10B shows a state where the respective members which form the artificial-blood-vessel connector 10B are mounted on the artificial blood vessel 20 and the respective members are mutually connected to each other. The configuration in the state shown in FIG. 10B is referred to as "artificial-blood-vessel unit 40 according to the embodiment 2" or is simply referred to as "artificial-blood-vessel unit 40".

In the artificial-blood-vessel connector 10B according to the embodiment 2, the connector portion 200 is integrally mounted on one end portion (an end portion on a side opposite to a connection portion to a living body side) of the cannula 90. Accordingly, the connection ring 100 used in the artificial-blood-vessel connector 10A according to the embodiment 1 becomes unnecessary.

In this manner, the structure of the connector portion 200 integrally mounted on one end portion of the cannula 90 is substantially equal to the structure of the connector portion 200 of the artificial-blood-vessel connector 10A according to the embodiment 1. Further, the structure of the ferrule 300 and the structure of the nut 400 are also equal to the structure of the ferrule 300 and the structure of the nut 400 of the artificial-blood-vessel connector 10A according to the embodiment 1. Accordingly, the same symbols are given to the identical parts respectively.

Steps of mounting the artificial-blood-vessel connector 10B according to the embodiment 2 on the artificial blood vessel 20 can be performed substantially in the same manner as the steps of mounting the artificial-blood-vessel connector 10A according to the embodiment 1 on the artificial blood vessel 20 and hence, the description of the steps is omitted. By mounting the artificial-blood-vessel connector 10B according to the embodiment 2 on the artificial blood vessel 20, an artificial-blood-vessel unit 40 according to the embodiment 2 is assembled (see FIG. 10B). In the embodiment 2, the connector portion 200 in the artificial-blood-vessel connector 10B is integrally formed with the cannula 90 and hence, in the artificial-blood-vessel unit 40 according to the embodiment 2, the artificial-blood-vessel unit 40 also includes the cannula 90.

Also in the artificial-blood-vessel connector 10B according to this embodiment, in fastening the nut 400 by making the female threaded portion 410 of the nut 400 (see FIG. 5A to 5C) threadedly engage with the male threaded portion 211 of the connector portion 200, in the same manner as the artificial-blood-vessel connector 10A according to the embodiment 1, the nut 400 is fastened while being rotated in a state where the nut 400 is not brought into direct contact with the artificial blood vessel 20 due to the presence of the ferrule 300. Accordingly, there is no possibility that a frictional force is applied to the artificial blood vessel 20 due to the rotation of the nut 400. As a result, it is possible to surely prevent a drawback that the artificial blood vessel is rubbed by a frictional force generated due to fastening the nut so that the artificial blood vessel is damaged.

Further, when the nut 400 is fastened, in the same manner as the artificial-blood-vessel connector 10A according to the embodiment 1, the ferrule 300 is made to slightly slide linearly toward the front side along the axial direction. In this sliding operation of the ferrule 300, an end portion e1 of a stepped portion S1 is also made to slide along an inclined outer peripheral surface portion 222 of the connector portion 200 while pressing the artificial blood vessel 20. Accordingly, as shown in FIG. 6B, in the artificial blood vessel 20, the raised portion 20a is formed on the front side of the stepped portion S1. Accordingly, even when the tensile force toward the rear side is applied to the artificial blood vessel 20, it is possible to surely prevent the artificial blood vessel 20 from being removed from the connector portion 200.

As has been described heretofore, according to the artificial-blood-vessel connector 10B according to the embodiment 2, in the same manner as the artificial-blood-vessel connector 10A according to the embodiment 1, it is possible to prevent a damage on an artificial blood vessel formed of a woven fabric made of resin fibers and, at the same time, it is possible to increase reliability in connection between the artificial blood vessel and the artificial-blood-vessel connector.

Further, according to the artificial-blood-vessel unit according to the embodiment 2, with the use of the artificial-blood-vessel connector 10B according to the embodiment 2 as the artificial-blood vessel connector, it is possible to provide the high-quality artificial blood vessel having no damages as the artificial blood vessel 20 which forms a part of the artificial-blood-vessel unit 40. Further, it is also possible to provide the artificial-blood-vessel unit which exhibits high reliability in connection between the artificial blood vessel 20 and the artificial-blood-vessel connector 10B.

In the artificial-blood-vessel connector 10B according to the embodiment 2, the case has been exemplified where the connector portion 200 is integrally mounted on the cannula 90. However, the connector portion 200 may be integrally mounted on a connecting fitting of a blood pump.

The present invention is not limited to the above-mentioned embodiments, and various modifications are conceivable without departing from the gist of the present invention. For example, the following modifications are conceivable.

(1) In the above-mentioned respective embodiments, the case has been exemplified where the ferrule 300 is provided with two pawl plate portions 320. However, the number of pawl plate portions 320 of the ferrule 300 is not limited to two, and may be three or more. For example, when the ferrule 300 is provided with three or more pawl plate portions, the pawl plate portions 320 are formed on the cylindrical portion 310 at intervals of 120 degrees in a circumferential direction of the cylindrical portion 310. When the ferrule 300 is provided with three pawl plate portions in this manner, flat surface portions 212 of the first cylindrical body portions 210 of the connector portion 200 are also formed at intervals of 120 degrees in a circumferential direction of the first cylindrical body portion 210.

(2) In the above-mentioned respective embodiments, the description has been made with respect to the case where the artificial blood vessel is an artificial blood vessel formed of a woven fabric made of resin fibers. However, the artificial-blood-vessel connector and the artificial-blood-vessel unit of the present invention are not limited to the artificial blood vessel formed of a woven fabric made of resin fibers, and are also applicable to artificial blood vessels made of other raw materials (for example, stretched porous polytetrafluoroethylene (ePTFE).

(3) The description has been made with respect to the case where the inclined angle θ2 of the inclined inner peripheral surface portion 312 of the cylindrical portion 310 of the ferrule 300 is equal to the inclined angle θ1 of the inclined outer peripheral surface portion 222 of the second cylindrical portion 220 of the connector portion 200. However, it is not always necessary to set the inclined angle θ2 of the inclined inner peripheral surface portion 312 equal to the inclined angle θ1 of the inclined outer peripheral surface portion 222. Provided that the stepped portion S1 is formed between the first flat inner peripheral surface portion 311 and the inclined inner peripheral surface portion 312, the inclined angle θ2 of the inclined inner peripheral surface portion 312 may be set smaller than the inclined angle θ1 of the inclined outer peripheral surface portion 222. When the inclined angle θ2 of the inclined inner peripheral surface portion 312 of the ferrule 300 is set smaller the inclined angle θ1 of the inclined outer peripheral surface portion 222 of the connector portion 200, the inclined angle θ2 of the inclined inner peripheral surface portion 312 may be set to 0 degrees. That is, it is sufficient that the inclined angle θ2 of the inclined inner peripheral surface portion 312 is set to a value which falls within a range of $0 \leq \theta 2 \leq \theta 1$.

In this manner, provided that the inclination angle of the inclined inner peripheral surface portion 312 of the ferrule 300 is set to a value which falls within a range of $0 \leq \theta 2 \leq \theta 1$ and the stepped portion S1 is present between the first flat inner peripheral surface portion 311 and the inclined inner peripheral surface portion 312, the end portion e1 of the stepped portion S1 is made to slightly slide along the inclined outer peripheral surface portion 222 of the connector portion 200 while pressing the artificial blood vessel 20. Accordingly, as shown in FIG. 6B, the raised portion 20a is formed on the artificial blood vessel 20 in front of the stepped portion S1. As a result, even when the tensile force toward the rear side is applied to the artificial blood vessel 20, it is possible to surely prevent the artificial blood vessel 20 from being removed from the connector portion 200 and hence, the reliability in connection between the artificial blood vessel 20 and the artificial-blood-vessel connector 10A can be further increased.

REFERENCE SIGNS LIST 10A, 10B: artificial-blood-vessel connector
20: artificial blood vessel
30, 40: artificial-blood-vessel unit
50: blood pump
90: cannula
100: connection ring
121, 430: inner extending portion
200: connector portion
210: first cylindrical body portion
211: male threaded portion
212: flat surface portion
220: second cylindrical body portion
221: first flat outer peripheral surface portion
222: inclined outer peripheral surface portion
223: second flat outer peripheral surface portion
230: flange portion
300: ferrule
310: cylindrical portion
311: first flat inner peripheral surface portion
312: inclined inner peripheral surface portion
313: second flat inner peripheral surface portion
314: notched portion
320: pawl plate portion
400: nut
410: female threaded portion
500: bending preventing member
e1: end portion of the stepped portion S1 on inclined inner peripheral surface portion 312 side (end portion of stepped portion S1)
S1: stepped portion θ1: inclination angle of the inclined outer peripheral surface portion 222
θ2: inclination angle of the inclined inner peripheral surface portion 312

The invention claimed is:

1. An artificial-blood-vessel connector for connecting an artificial blood vessel to an object to be connected by being mounted on the artificial blood vessel, wherein assuming a side of the artificial-blood-vessel connector which faces the object to be connected as a front side, a side of the artificial-blood-vessel connector opposite to the front side as a rear side, and a direction along which a center axis of the artificial blood vessel extends as an axial direction, the artificial-blood-vessel connector comprises:
 a connector portion which includes: a first cylindrical body portion where a male threaded portion and a flat surface portion where the male threaded portion is not formed are alternately formed along a circumferential direction of an outer peripheral surface; and a second cylindrical body portion which is formed on a rear-side end portion of the first cylindrical body portion, has an outer diameter smaller than an outer diameter of the first cylindrical body portion, and is configured to be fitted into the inside of the artificial blood vessel;
 a ferrule which includes: a cylindrical portion which is configured to be fitted on an outer peripheral surface of the second cylindrical body portion by way of the artificial blood vessel by being made to slide linearly toward the front side on a surface of the artificial blood vessel in a state where the second cylindrical body portion of the connector portion is fitted in the artificial blood vessel; and a pawl plate portion which is formed in a projecting manner along the axial direction from the cylindrical portion, and is brought into contact with the flat surface portion of the first cylindrical body portion; and
 a nut which includes a female threaded portion which is configured to threadedly engage with the male threaded portion of the first cylindrical body portion of the connector portion, and is configured to be connected to the connector portion by making the female threaded portion threadedly engage with the male threaded portion of the first cylindrical body portion in a state where the nut covers the ferrule when the second cylindrical body portion is fitted in the artificial blood vessel and the ferrule is mounted on the connector portion.

2. The artificial-blood-vessel connector according to claim 1, wherein the second cylindrical body portion of the connector portion includes:
 a first flat outer peripheral surface portion which has an outer diameter of an outer peripheral surface thereof set to a fixed value in an axial direction;
 an inclined outer peripheral surface portion which is formed continuously with the first flat outer peripheral surface portion, an outer peripheral surface of the inclined outer peripheral surface portion having a diameter thereof gradually narrowed in a tapered shape in a direction toward the rear side from the first flat outer peripheral surface portion; and
 a second flat outer peripheral surface portion which is formed continuously with the inclined outer peripheral surface portion, an outer diameter of an outer peripheral surface of the second flat outer peripheral surface portion being fixed in the axial direction, wherein the ferrule includes, on an inner peripheral surface of the cylindrical portion thereof:
 a first flat inner peripheral surface portion which corresponds to the first flat outer peripheral surface portion of the second cylindrical body portion and has an inner diameter of an inner peripheral surface thereof set to a fixed value in the axial direction; an inclined inner peripheral surface portion which corresponds to the inclined outer peripheral surface portion of the second cylindrical body portion; and a second flat inner peripheral surface portion which corresponds to the second flat outer peripheral surface portion of the second cylindrical body portion and has an inner diameter of an inner peripheral surface thereof set to a fixed value in the axial direction, wherein assuming an inclination angle of the inclined outer peripheral surface portion as θ1 and an inclination angle of the inclined inner peripheral surface portion as θ2, the inclined angle θ2 of the inclined inner peripheral surface portion is set to a value which falls within a range of $0 \leq \theta 2 \leq \theta 1$, and a stepped portion is formed on a boundary between the first flat inner peripheral surface portion and the inclined inner peripheral surface portion, and
 the stepped portion is formed such that an end portion of the stepped portion on an inclined inner peripheral surface portion side is positioned in the middle of the inclined outer peripheral surface portion of the connector portion when the ferrule is brought into a state where the ferrule is mounted on the connector portion such that the pawl plate portion of the ferrule is brought into contact with the flat surface portion of the first cylindrical body portion.

3. The artificial-blood-vessel connector according to claim 2, wherein the nut has a pressing force applying portion which applies a pressing force for linearly sliding the ferrule toward the front side to the ferrule at the time of connecting the nut to the connector portion, and the ferrule has a pressing force receiving portion which receives the pressing force of the nut, and
 the ferrule is configured to perform an operation where the ferrule is made to linearly slide toward the front side by receiving the pressing force of the nut so that the end portion of the stepped portion on the inclined inner peripheral surface portion side is made to slide along the inclined outer peripheral surface portion of the connector portion while pressing the artificial blood vessel.

4. The artificial-blood-vessel connector according to claim 3, wherein
 the pressing force applying portion which the nut has is an inner extending portion which is formed on a rear-side end portion of the nut in a circumferential direction such that the inner extending portion projects in a radially inward direction, and the pressing force receiving portion which the ferrule has is a notched portion formed on a rear-side end portion of the cylindrical portion of the ferrule along the circumferential direction, and is configured to bring the inner extending portion into contact with the notched portion.

5. The artificial-blood-vessel connector according to claim 1, further comprising a connection ring connectable to the object to be connected, the connection ring having a female threaded portion on an inner peripheral surface thereof so as to connect the connector portion to the object to be connected by making the female threaded portion of the connection ring threadedly engage with a male threaded portion formed on an object-to-be-connected side.

6. The artificial-blood-vessel connector according to claim 1, further comprising a bending preventing member which prevents sharp bending of the artificial blood vessel at a rear-side end portion of the nut.

7. The artificial-blood-vessel connector according to claim 1, wherein the artificial blood vessel is an artificial blood vessel formed of a woven fabric made of resin fibers.

8. The artificial-blood-vessel connector according to claim 1, wherein the object to be connected is a blood pump or a cannula.

9. An artificial-blood-vessel unit comprising:
   an artificial blood vessel formed of a woven fabric made of resin fibers; and an artificial-blood-vessel connector for connecting the artificial blood vessel to an object to be connected, the artificial-blood-vessel connector being mounted on the artificial blood vessel, wherein
   the artificial-blood-vessel connector is the artificial-blood-vessel connector according to claim 1.

\* \* \* \* \*